United States Patent
Takagi et al.

(10) Patent No.: US 7,144,726 B2
(45) Date of Patent: *Dec. 5, 2006

(54) APPARATUS FOR CULTURING CELL/TISSUE

(75) Inventors: Takao Takagi, Fuji (JP); Setsuo Watanabe, Fuji (JP)

(73) Assignee: Takagi Industrial Co., Fuji (JP)

( * ) Notice: Subject to any disclaimer, the term of this patent is extended or adjusted under 35 U.S.C. 154(b) by 144 days.

This patent is subject to a terminal disclaimer.

(21) Appl. No.: 10/499,304

(22) PCT Filed: Nov. 19, 2002

(86) PCT No.: PCT/JP02/12084

§ 371 (c)(1),
(2), (4) Date: Jun. 18, 2004

(87) PCT Pub. No.: WO03/054137

PCT Pub. Date: Jul. 3, 2003

(65) Prior Publication Data

US 2005/0106716 A1    May 19, 2005

(30) Foreign Application Priority Data

Dec. 12, 2001   (JP)   ............................. 2001-389549

(51) Int. Cl.
*C12M 1/36* (2006.01)

(52) U.S. Cl. ................. 435/286.6; 435/288.3; 435/288.7

(58) Field of Classification Search ............... None
See application file for complete search history.

(56) References Cited

U.S. PATENT DOCUMENTS

| | | | |
|---|---|---|---|
| 5,330,908 A | | 7/1994 | Spaulding |
| 5,928,945 A | | 7/1999 | Seliktar et al. |
| 6,037,141 A | * | 3/2000 | Banes .................. 435/30 |
| 6,586,235 B1 | * | 7/2003 | Banes .................. 435/293.1 |

FOREIGN PATENT DOCUMENTS

| | | |
|---|---|---|
| AU | 744686 B | 6/1998 |
| JP | 50-5599 A | 1/1975 |
| JP | 2001-504697 | 4/2001 |
| WO | WO-98-22573 A1 | 5/1998 |

* cited by examiner

*Primary Examiner*—David Redding
(74) *Attorney, Agent, or Firm*—Connolly Bove Lodge & Hutz LLP

(57) ABSTRACT

A cell/tissue culture apparatus can give a physical stimulation necessary for proliferation and growth to a cultured object which is a cell or tissue to be cultured. The cell/tissue culture apparatus has a chamber (a culture chamber 4) which accommodates a cultured object (a matrix 8) and supplies a culture fluid (6), a pressing means (a pressing plate 10, 11) which is movably arranged in the chamber and gives a physical stimulation due to a press to the cultured object by movement thereof, and a driving means (a pressure unit 22, an electromagnet unit 32) which gives a driving force to the pressing means for applying the physical stimulation to the cultured object from an outside of the chamber in a state out of contact with the pressing means.

4 Claims, 10 Drawing Sheets

APPARATUS FOR CULTURING CELL/TISSUE

TECHNICAL FIELD

The present invention relates to a cell/tissue culture apparatus used for a culture of a cell or tissue, to which tissue engineering is applied. More particularly, the present invention relates to a cell/tissue culture apparatus for efficiently realizing a metabolism function of a cell or tissue when performing an in vitro culture of a cell or tissue of a living body of a human body and for giving a physical stimulation necessary for prolongation, differentiation and promotion of a cell to an cultured object.

BACKGROUND ART

In a conventional method which performs an in vitro culture of a cell or tissue of a living body of a human body there is employed a method in which temperature, humidity, the concentration of carbon dioxide and the concentration of oxygen in an incubator are maintained at proper conditions, and a cell is cultured in that incubator. A cell or tissue is placed in a culture fluid in a floating state, or a cell or tissue is fixed to an inside or a surface of a gel in which an ingredient of the culture fluid is input, and thereby, the cell or tissue is made to proliferate and to grow. Or, a cell or tissue is transplanted in a material, which is called a matrix or a scaffold, a carrier or a mold, and so on (herein after called "matrix" simply), and thereby, the cell or tissue is made to proliferate and to grow.

By the way, for the proliferation and growth of a cell or tissue, it is important to give a physical stimulation to a cell or tissue to be cultured in addition to environmental conditions of temperature, humidity, the concentration of carbon dioxide, and the concentration of oxygen, Such a physical stimulation is an indispensable factor for promoting differentiation and growth of a cell or tissue and for growing to a cell or tissue closer to a cell or tissue in a living body. As a technology which gives a physical stimulation to the proliferation and growth of a cell or tissue, there is, for example, the Japanese Official Announcement Patent Publication No. 2001-504697 entitled "APPLICATION OF SHEAR FLOW STRESS TO CHONDROCYTES".

The present invention, therefore, makes it an object to provide a cell/tissue culture apparatus capable of giving a physical stimulation necessary for proliferation and growth to a cultured object which is a cell or tissue to be cultured.

DISCLOSURE OF THE INVENTION

A composition of a cell/tissue culture apparatus of the present invention which attains the above object is as follows.

The cell/tissue culture apparatus of the present invention makes it a feature to have a chamber (a culture chamber 4) which accommodates a cultured object (a matrix 8) and supplies a culture fluid (6), a pressing means (a pressing plate 10, 11) which is movably placed in the chamber and gives a physical stimulation due to a press to said cultured object by movement thereof, and a driving means (a pressure unit 22, an electromagnet unit 32) which gives a driving force to said pressing means for giving said physical stimulation to said cultured object from an outside of said chamber in a state out of contact with the pressing means.

In the cell/tissue culture apparatus of the present invention, said physical stimulation makes it a feature to be a compressive force.

In the cell/tissue culture apparatus of the present invention, said driving means makes it a feature to give said driving force to said pressing means by means of magnetic coupling between said pressing means and said driving means.

In the cell/tissue culture apparatus of the present invention, said chamber makes it a feature to make a part or the whole of a member constituting said chamber transparent so that said cultured object of its inside can be visually recognized from an outside.

According to the above-mentioned composition, it is possible to give a physical stimulation due to desired press-compression from an outside to a cultured object. In this case, although the cultured object namely a cell or tissue to which a pressing force is applied in one direction is compressed in a direction of the pressing force, the cultured object becomes a state of elongation in a direction which is at right angles with a compressive direction. Further, if the pressing force is cancelled, the cultured object is to return to a former shape. Since the cultured object to which a physical stimulation due to press-compression like this is applied is to receive stimulation similar to a human body, its growth is promoted. Furthermore, since a culture fluid is given to the cultured object, it is possible to give necessary nourishment.

Therefore, according to the cell/tissue culture apparatus of the present invention, it is possible to give compression due to a desired pressing force or a physical stimulation due to its cancellation to a cell or tissue to be cultured, and it is possible to promote a culture.

Furthermore, by making a part or the whole of a member constituting the chamber transparent and making it possible to visually recognize from an outside, it is possible to observe the growth of a cultured object with ease.

And, the objects, features, advantages and so on of the present invention will be more precise by referring to an explanation in the modes for carrying out the present invention and the embodiments shown in the drawings.

BEST MODES FOR CARRYING OUT THE INVENTION

Figure 1:
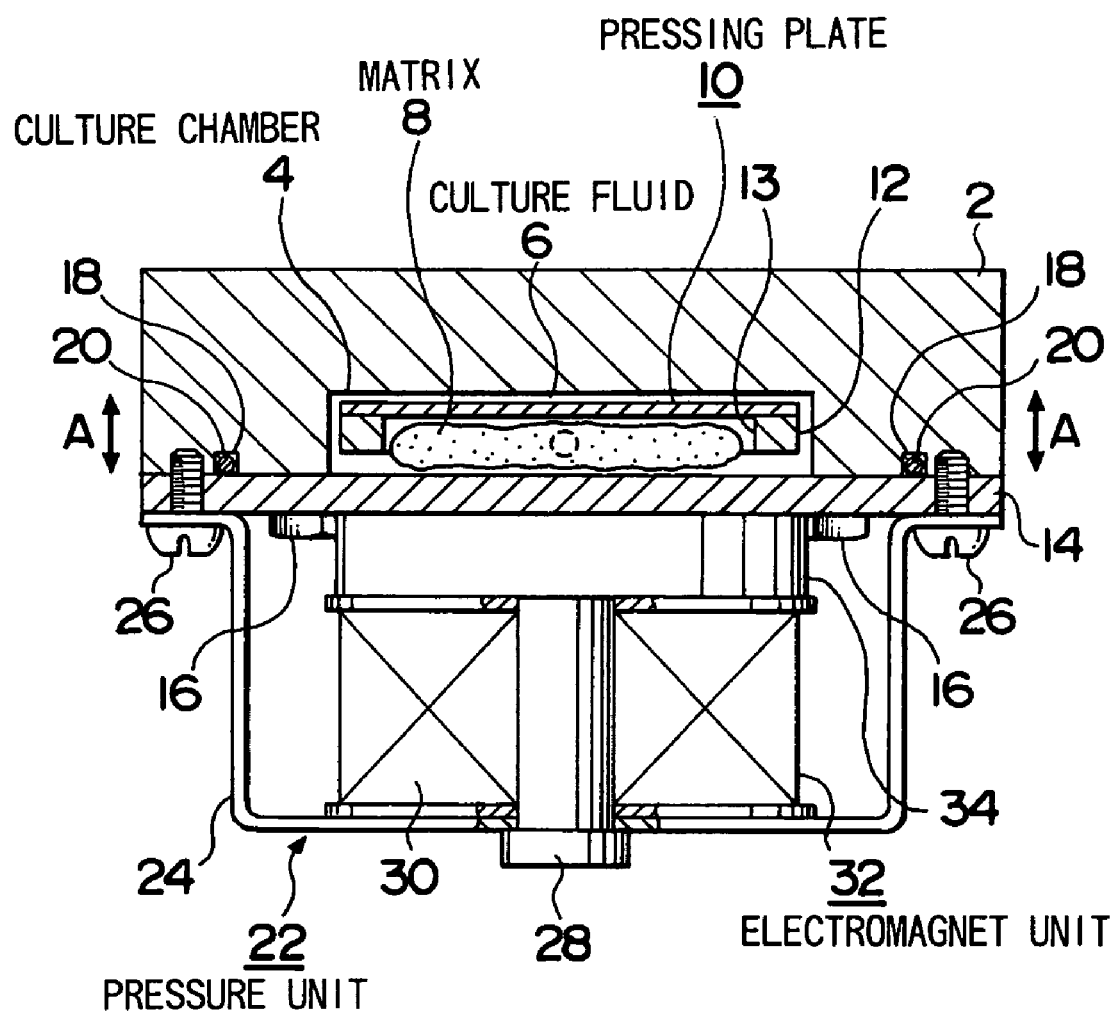
FIG. 1 is a longitudinal sectional view showing a first embodiment of a cell/tissue culture apparatus according to the present invention.

In the following, the present invention and its modes for carrying out the present invention are explained by referring to embodiments shown in the drawings.

FIG. 1 shows a first embodiment of a cell/tissue culture apparatus according to the present invention.

For example, a disk-shaped chamber body 2 is installed, and a culture chamber 4 which is a circular culture space is formed inside the chamber body 2. To an inside of the culture chamber 4, a matrix 8 as a cultured object in which a cell of a patient has been transplanted is placed together with a culture fluid 6, and a pressing plate 10 is provided as a pressing means of the matrix 8. For the matrix 8, a thing formed by a protein and so on which are united into a tissue according to the growth of a cell, for example, a sponge is used.

Figure 2:
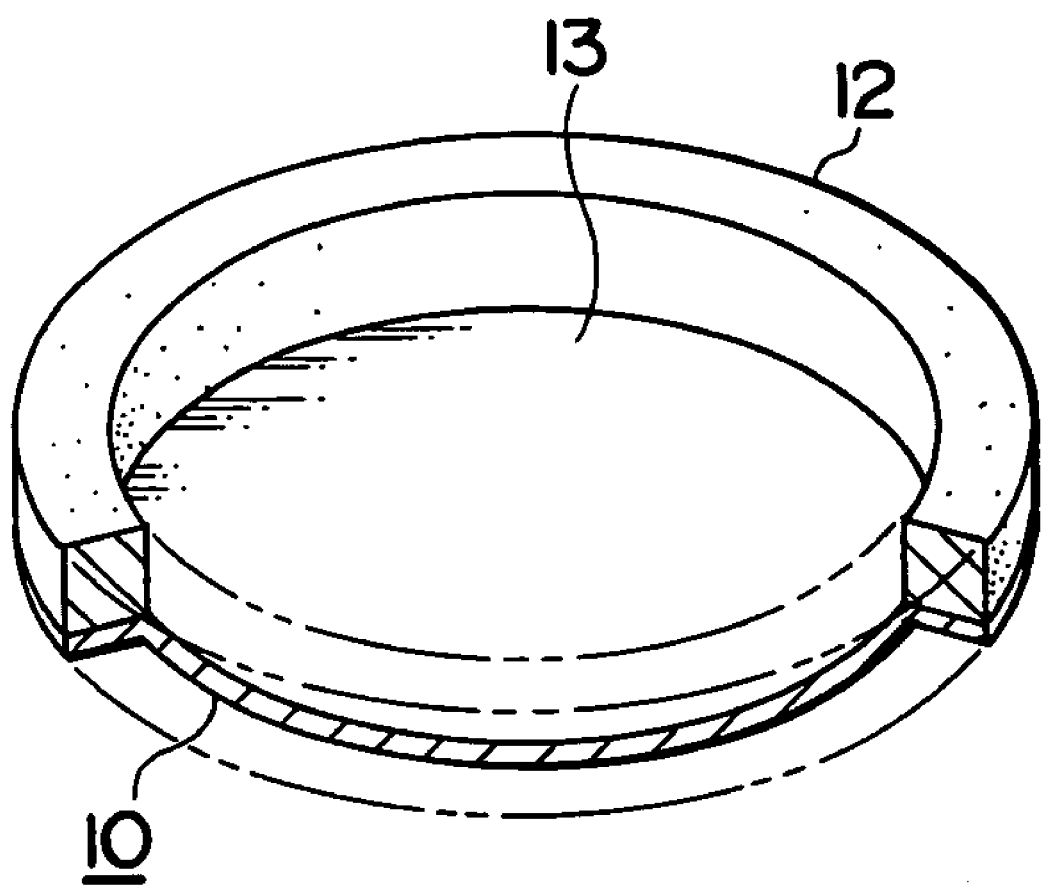
FIG. 2 is a perspective view showing a pressing plate of which a part is nicked.

For example, as shown in FIG. 2, the pressing plate 10 is a disk shape, and a magnetic annular portion 12 of wall thickness is formed a circumferential part. In this embodiment, the matrix 8 is placed in a space portion 13 surrounded with the magnetic annular portion 12, and the magnetic annular portion 12 is formed by a magnetic material.

Figure 3:
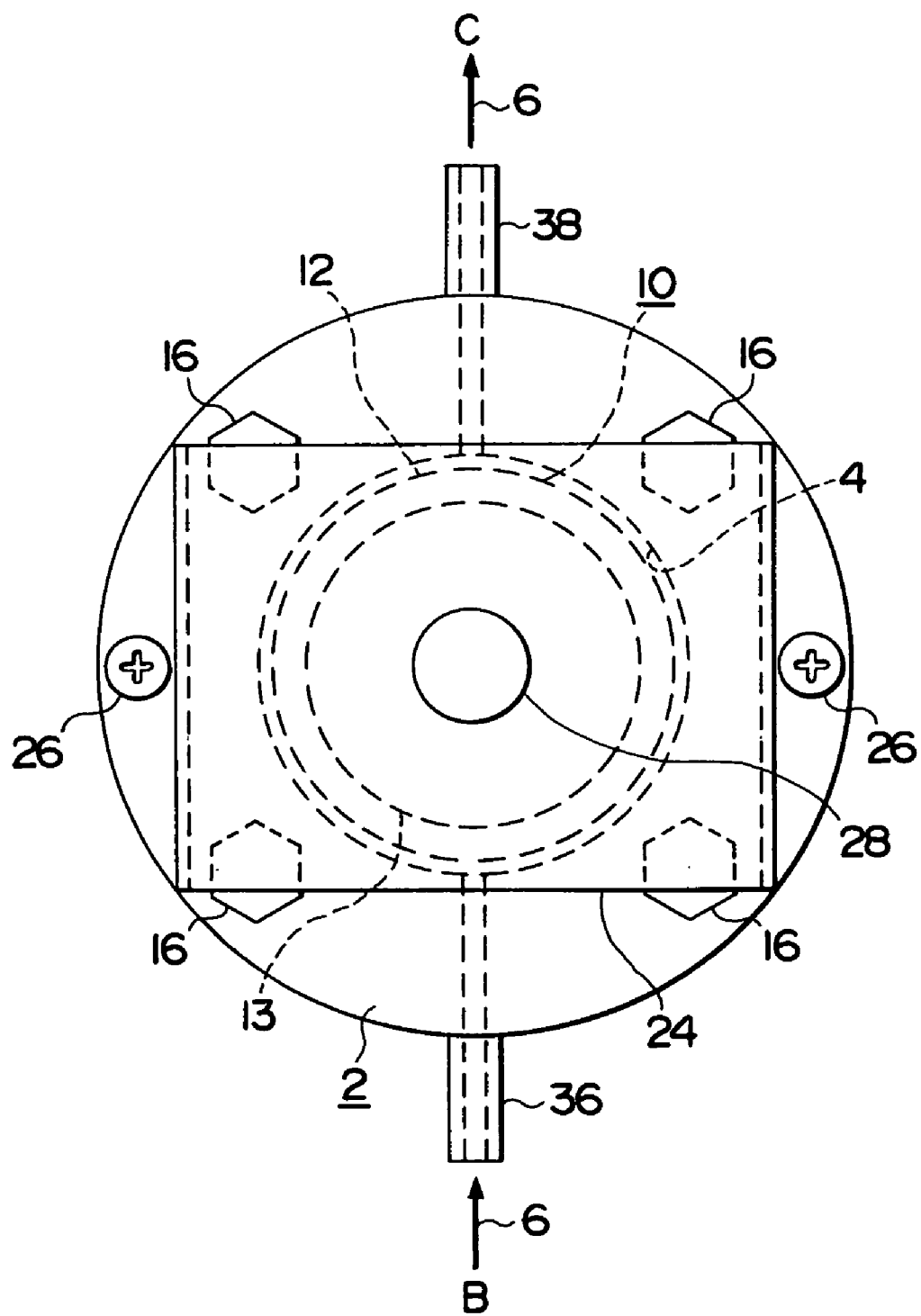
FIG. 3 is a rear view showing the cell/tissue culture apparatus of the present invention.

To the chamber body 2, a chamber hatch plate 14 serving as a means which blockades the culture chamber 4 is fixed by a plurality of block bolts 16 (FIG. 3) which are a fixing means. In a portion between the chamber hatch plate 14 and the chamber body 2, an O-ring 20 which is a sealing means is provided at a recess portion 18 of a side of the chamber body 2, and thereby, a high air-tightness is maintained.

In a side of the chamber hatch plate 14, a pressure unit 22 serving as a driving means which presses by making the pressing plate 10 go up and down in the drawing as shown in an arrow A is installed. That is, a mounting plate 24 formed in a U-shape is attached to the chamber hatch plate 14 by fixing screws 26, and an electromagnet unit 32 in which a solenoid 30 is wound around a core 28 formed by a magnetic material is attached to the mounting plate 24 by making a back end portion of the core 28 pierce the mounting plate 24.

In order to make a magnetic force apply to the magnetic annular portion 12 or the pressing plate 10 formed by a magnetic material, a magnetic field generation part 34 which has an area or a shape corresponding to the magnetic annular portion 12 or the pressing plate 10 is formed to the core 28. This magnetic field generation part 34 is installed with a state adhering closely to the chamber hatch plate 14 in order to heighten magnetic efficiency. That is, in this embodiment, the magnetic annular potion 12 of a side of the pressing plate 10 and the electromagnet unit 32 are in a state of magnetic coupling through the chamber hatch plate 14. Because of this, a magnetic driving force (an attractive force or a repulsive force) can be generated for the pressing plate 10 by a DC magnetic field or AC magnetic field which the electromagnet unit 32 generates, and, by this, it is possible to apply a pressing force to the matrix 8.

Further, to the chamber body 2, culture fluid ports 36 and 38 for circulating the culture fluid 6 in the culture chamber 4 are formed at corresponding positions in the direction of its diameter. To each of the culture fluid ports 36 and 38, a culture circuit not shown in the drawings is connected. The pure culture fluid 6 is supplied to the culture fluid port 36 as shown by an arrow B, and, after circulating in the culture chamber 4, it flows out of the culture fluid port 38 as shown by an arrow C.

Figure 4:
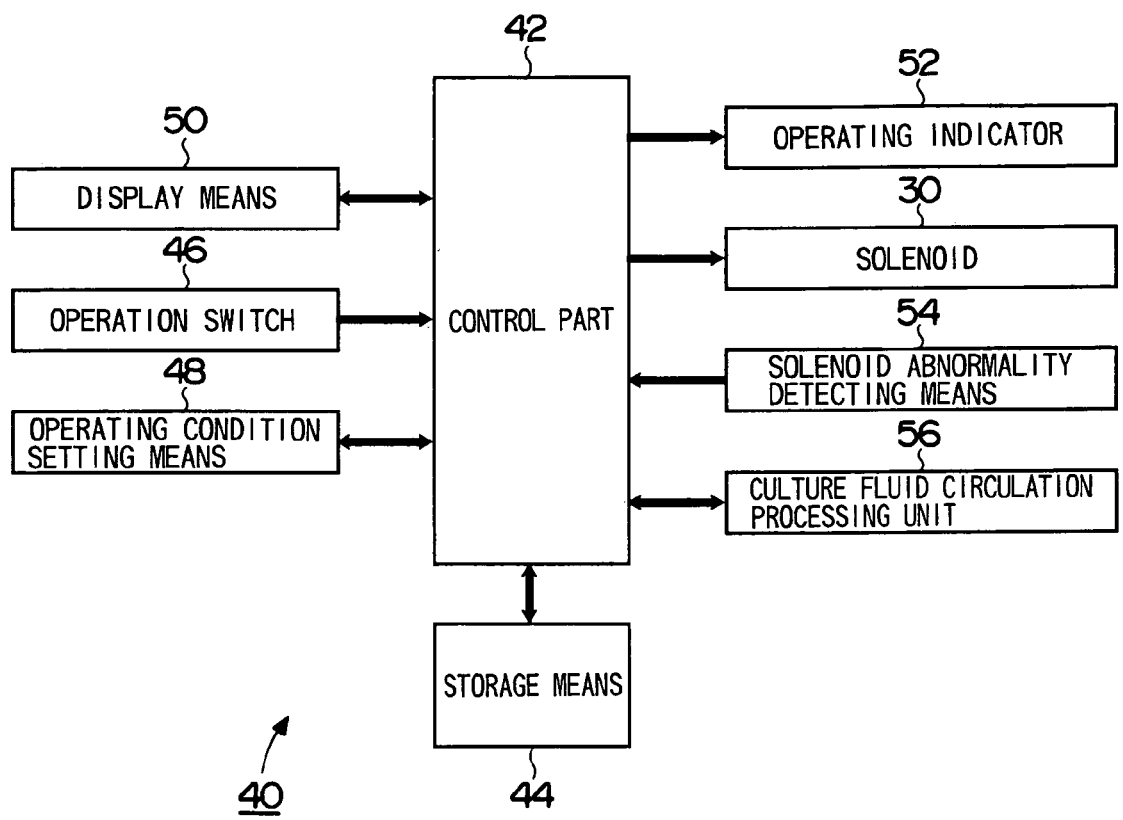
FIG. 4 is a block diagram showing a control device.

Furthermore, for this cell/tissue culture apparatus, as a culture control means, for example, a culture control device 40 shown in FIG. 4 is installed, and a control part 42 is provided as an arithmetic/control means. To this control part 42, a storage means 44 which stores data and a control program is connected. Along with this, a solenoid 30, an operation switch 46 which orders a start of operation, an operating condition setting means 48 for setting an operating condition, a display means 50 which displays an operating state, and an operating indicator 52 which performs indication under an operation are connected. Further, a solenoid abnormality detecting means 54 which detects a state of abnormality of disconnection, temperature abnormality and so on of the solenoid 30, and a culture fluid circulation processing unit 56 which performs supply of the culture fluid 6 to the culture chamber 4 and control thereof are connected.

Figure 5:
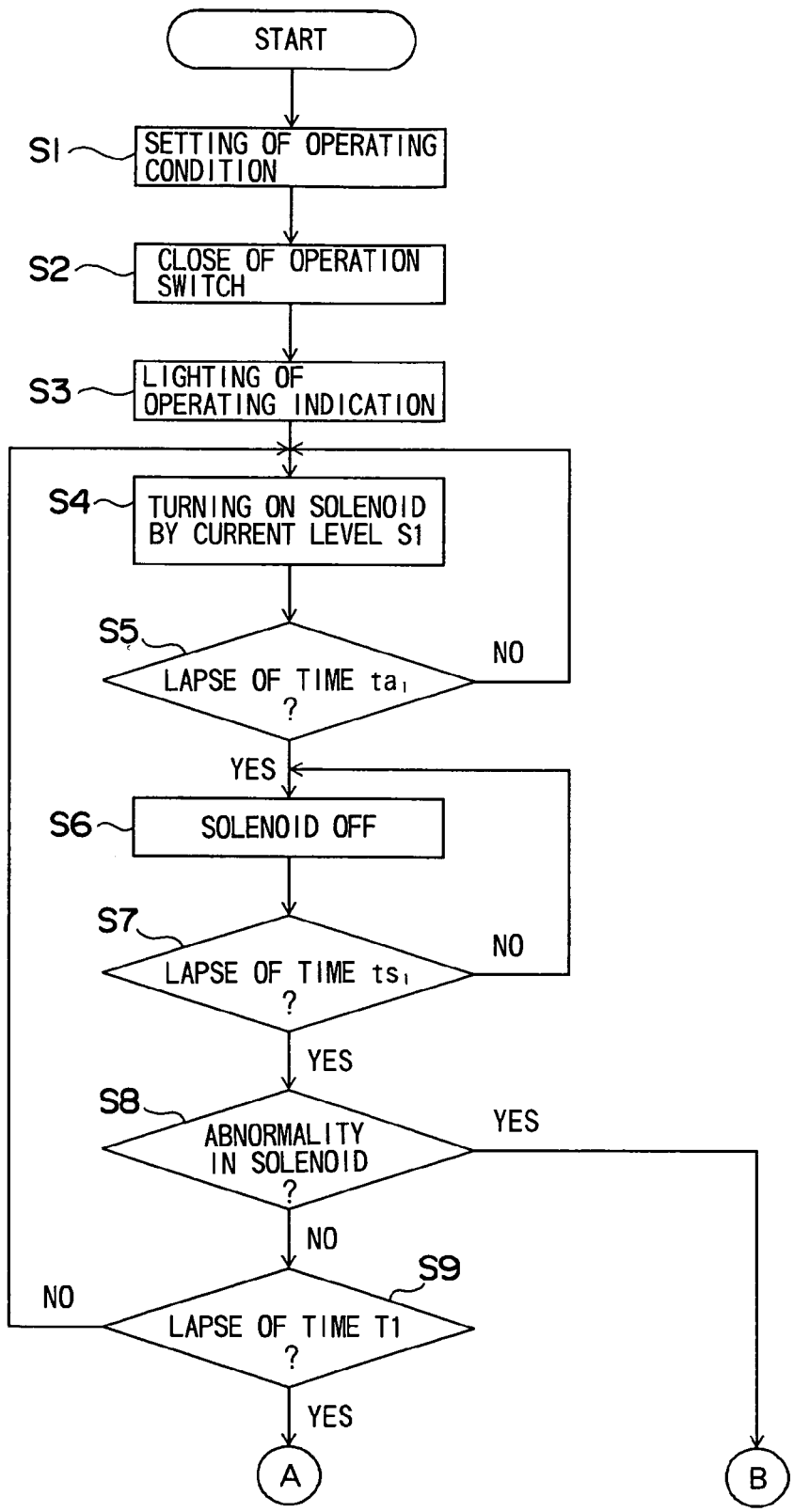
FIG. 5 is a flow chart showing a part of the former half of a control program.
Figure 6:
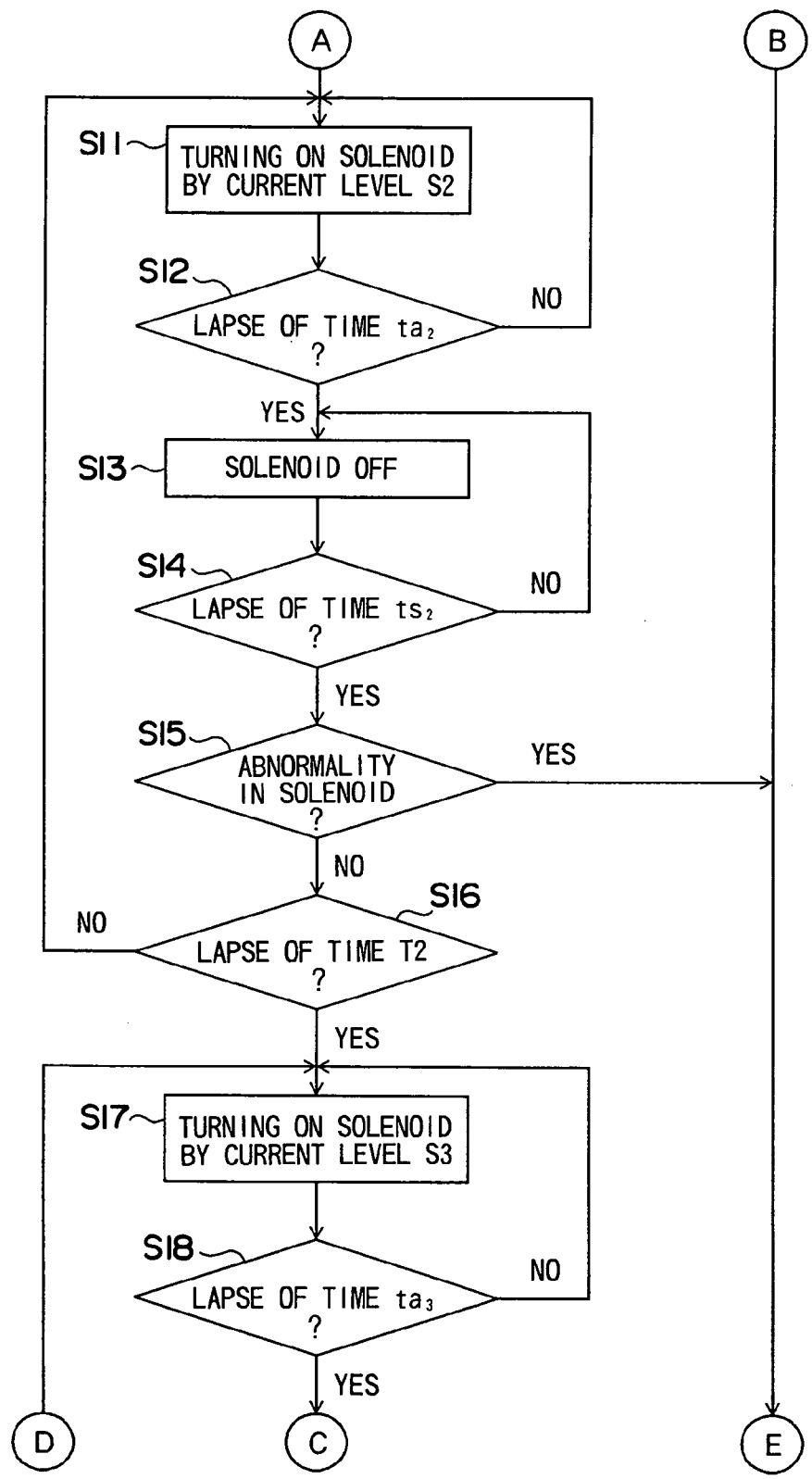
FIG. 6 is a flow chart showing a control program continued on FIG. 5.
Figure 7:
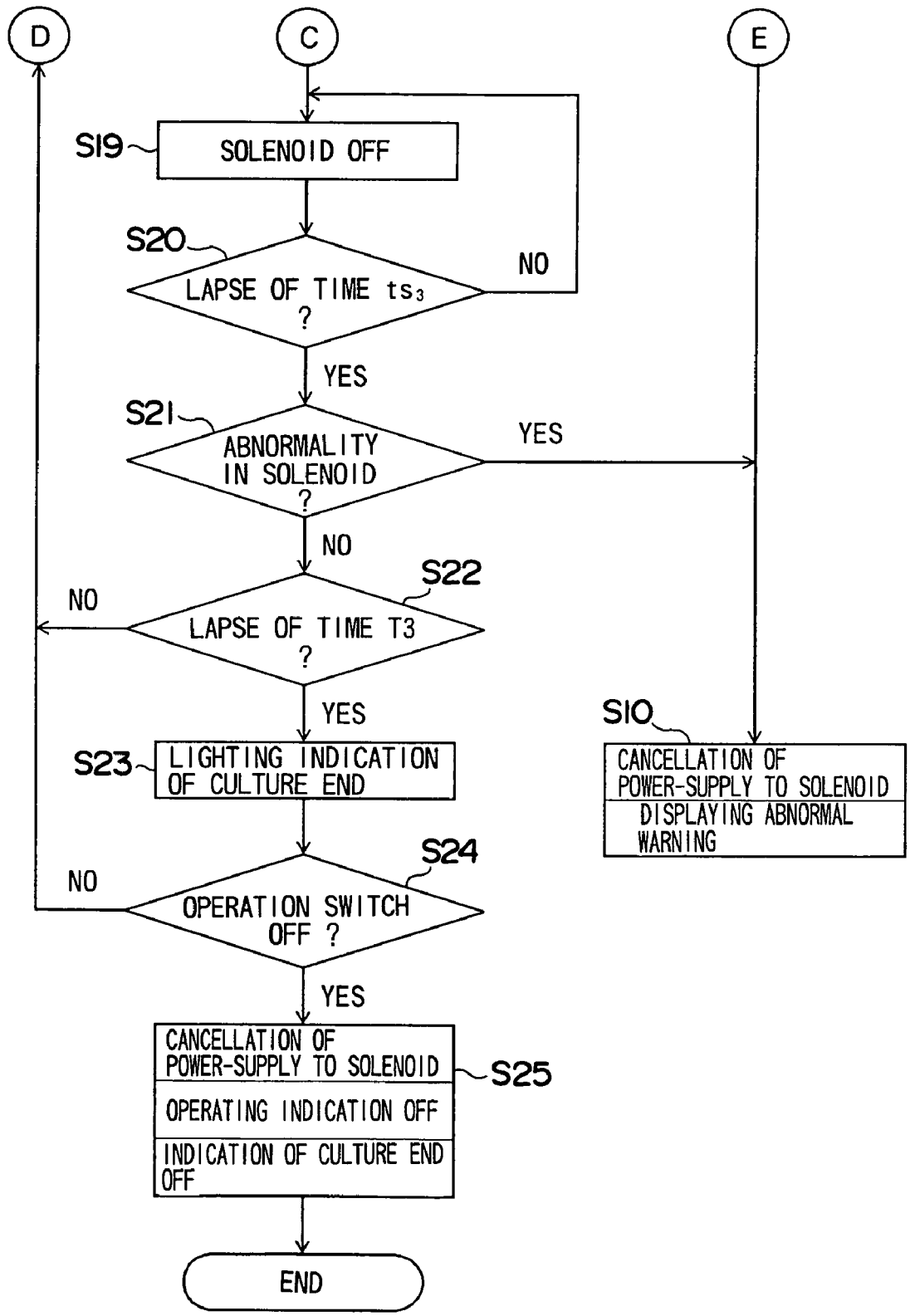
FIG. 7 is a flow chart showing a part of the latter half of a control program continued on FIG. 6.

Next, culture processing is explained by referring to flow charts in FIG. 5 through FIG. 7. In FIG. 5 through FIG. 7, reference letters A, B, C, D and E show connectors.

After the matrix 8 in which a cell or tissue to be cultured is planted is placed in the culture chamber 4, the culture fluid 6 is supplied from the culture fluid port 36, and the culture fluid 6 is made to circulate in the culture chamber 4. A step S1 is a setting process of a plurality of operating conditions. In this embodiment, operating conditions of three stages are set through the operating condition setting means 48, and setting of a driving force of the solenoid 30 is performed. For example, for operating conditions, there are current levels S1, S2 and S3 which set a pressing force of the pressing plate 10 (magnitude of each level is optional, for example, S1<S2<S3), holding times $ta_1$, $ta_2$ and $ta_3$ (width of each time is optional, for example, $ta_1<ta_2<ta_3$), releasing times $ts_1$, $ts_2$ and $ts_3$ (width of each time is optional, for example, $ts_1<ts_2<ts_3$), continuation times T1, T2 and T3 (width of each time is optional, for example, T1<T2<T3), and so on. The magnitude and time width of stimulation can be increased and decreased with the lapse of time. It goes without saying that they can be set to an optional value, and it is possible to vary them according to the state of affairs in a culture.

After setting of operating conditions like this, if a close of the operation switch 46 is detected at a step S2, an operation is started. At a step S3, the operating indicator 52 is lighted up and a start of the operation is indicated.

In this embodiment, at a step S4, a current of the current level S1 is supplied to the solenoid 30, and the solenoid 30 is excited. At this time, the core 28 is magnetized, the magnetic annular portion 12 of the pressing plate 10 is attracted to a side of the magnetic field generation part 34 by a magnetic force of the current level S1, and the matrix 8 is pressed. At a step S5, a time of an ON state of the solenoid 30 is measured, and a pressing state is maintained for the holding time $ta_1$. The processing proceeds to a step S6 after the lapse of the holding time $ta_1$, and the solenoid 30 is released from magnetization. A step S7 represents the measurement of a releasing time, and a state of non-magnetization of the solenoid 30, namely a releasing state of the solenoid 30, is continued until the releasing time $ts_1$ elapses. At this time, the matrix 8 is released from the pressing state and returns to a natural state by elasticity of itself. In this case, if a pressing force by the pressing plate 10 is given in one direction of the matrix 8 which is a cultured object, namely, if the pressing force is given in direction of thickness in this embodiment, the matrix 8 and a cell or tissue are compressed in the direction of the pressing force, namely, the matrix 8 and the cell or tissue are compressed in an up and down direction in this embodiment. However, the matrix 8 and the cell or tissue become a state of elongation in a direction which is at right angles with the compressive direction, namely in a surface direction of the matrix 8. Further, if the pressing force is cancelled, the matrix 8 and the cell or tissue are to return to a former shape. Because of this, stimulation similar to the case of a living body is given to the matrix 8 and the cell or tissue by an intermittent repetition of a physical stimulation due to pressing and cancellation thereof, and the promotion of a culture is given.

Further, at a step S8, disconnection or temperature abnormality of the solenoid 30 is judged based on a detected output of the solenoid abnormality detecting means 54. The processing proceeds to a step S9 when abnormality is not detected, and whether or not the continuation time T1 elapses is decided. That is, the process of a setting condition 1 is maintained until the continuation time T1 elapses, and the processes of the steps S4 through S9 are continuously performed. Furthermore, in the continuation time T1, in case in which abnormality is detected at the step S8, the processing proceeds to a step S10. At the step S10, the cancellation of power-supply to the solenoid 30 is performed, and, along with this, the display of an abnormal warning is performed on the display means 50 and the occurrence of abnormality is notified.

When the continuation time T1 elapses, the processing proceeds to a step S11. At the step S11, a current of the current level S2 is supplied to the solenoid 30, and the solenoid 30 is excited. At this time, the core 28 is magnetized, the magnetic annular portion 12 of the pressing plate 10 is attracted to the side of the magnetic field generation part 34 by a magnetic force of the current level S2, and the matrix 8 is pressed. At a step S12, a time of an ON state of the solenoid 30 is measured, and a pressing state is kept up for the holding time $ta_2$. The processing proceeds to a step S13 after the lapse of the holding time $ta_2$, and the solenoid 30 is released from magnetization. A step S14 represents the measurement of a releasing time, and a state of non-magnetization of the solenoid 30, namely a releasing state of the solenoid 30, is continued until the releasing time $ts_2$ elapses. At this time, the matrix 8 is released from the pressing state and returns to the natural state by the elasticity of itself.

Further, at a step S15, disconnection or temperature abnormality of the solenoid 30 is judged based on a detected output of the solenoid abnormality detecting means 54. The processing proceeds to a step S16 when abnormality is not detected, and whether or not the continuation time T2 elapses is decided. That is, the process of a setting condition 2 is maintained until the continuation time T2 elapses, and the processes of the steps S11 through S16 are continuously performed. Furthermore, in the continuation time T2, in case in which abnormality is detected at the step S15, the processing proceeds to the step S10. At the step S10, the cancellation of power-supply to the solenoid 30 is performed, and, along with this, the display of an abnormal warning is performed on the display means 50 and the occurrence of abnormality is notified.

When the continuation time T2 elapses, the processing proceeds to a step S17. At the step S17, a current of the current level S3 is supplied to the solenoid 30, and the solenoid 30 is excited. At this time, the core 28 is magnetized by a current level of the current level S3, the magnetic annular portion 12 of the pressing plate 10 is attracted to the side of the magnetic field generation part 34 by its magnetic force, and the matrix 8 is pressed. At a step S18, a time of an ON state of the solenoid 30 is measured, and a pressing state is maintained for the holding time $ta_3$. The processing proceeds to a step S19 after the lapse of the holding time $ta_3$, and the solenoid 30 is released from magnetization. A step S20 represents the measurement of a releasing time, and a state of non-magnetization of the solenoid 30, namely a releasing state of the solenoid 30, is continued until the releasing time $ts_3$ elapses. At this time, the matrix 8 is released from the pressing state and returns to the natural state by the elasticity of itself.

Further, at a step S21, disconnection or temperature abnormality of the solenoid 30 is judged based on a detected output of the solenoid abnormality detecting means 54. The processing proceeds to a step S22 when abnormality is not detected, and whether or not the continuation time T3 elapses is decided. That is, the process of a setting condition 3 is maintained until the continuation time T3 elapses, and the processes of the steps S17 through S22 are continuously performed. In addition, in the continuation time T3, in case in which abnormality is detected at the step S21, the processing proceeds to the step S10. At the step S10, the cancellation of power-supply to the solenoid 30 is performed, and, along with this, the display of an abnormal warning is performed on the display means 50 and the occurrence of abnormality is notified.

Further, when the continuation time T3 elapses at the step S22, the processing proceeds to a step S23, and the indication of a culture end is lighted on the operating indicator 52. After informing the culture end, whether or not the operation switch 46 is switched to OFF is decided at a step S24. Then, at a step S25, the power-supply to the solenoid 30 is cancelled, the operating indication is turned OFF, the indication of the culture end is switched to OFF, and all operations are ended.

Figure 8:
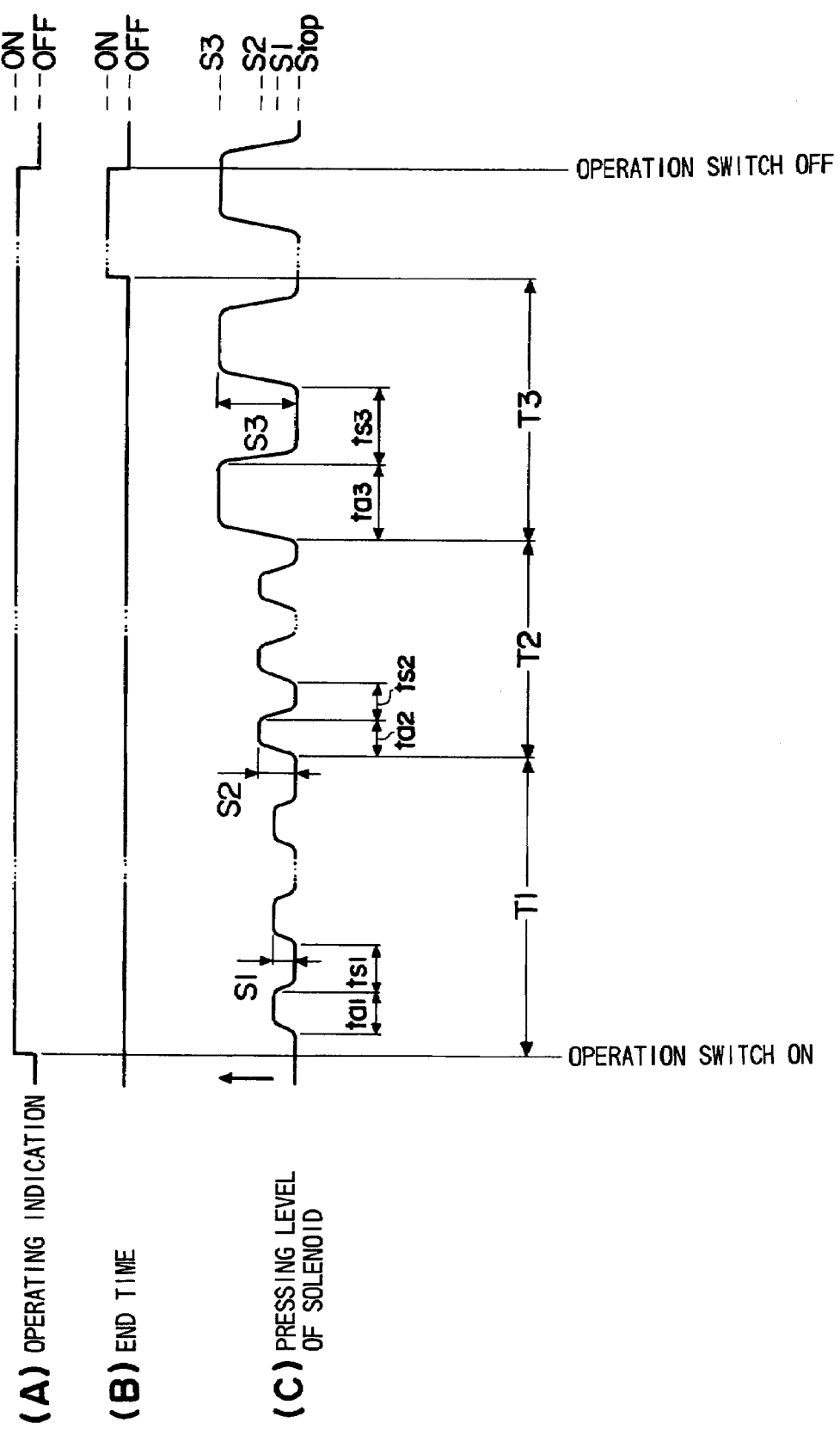
FIG. 8 is a timing chart showing a pressing action.

Furthermore, in FIG. 8, a reference letter (A) shows the operating indication on the action of the culture program, a reference letter (B) shows the end indication, and a reference letter (C) shows the repetition of a pressing force which is applied to the matrix 8 from the pressing plate 10 by means of a generated magnetic field of the solenoid 30. As shown in FIG. 8, in this embodiment, a pressing force level by means of the solenoid 30 is set to S1, S2 and S3, and a desired acceleration and deceleration control is performed by repetition thereof.

According to such a culture program, it is possible to produce a tissue equivalent to the cartilage of a joint on which a compressive force works in a certain direction, especially, equivalent to a muscle and a cartilage of loins and a knee, and it is possible to use for the restoration of a deficient portion of a patient.

Figure 9:
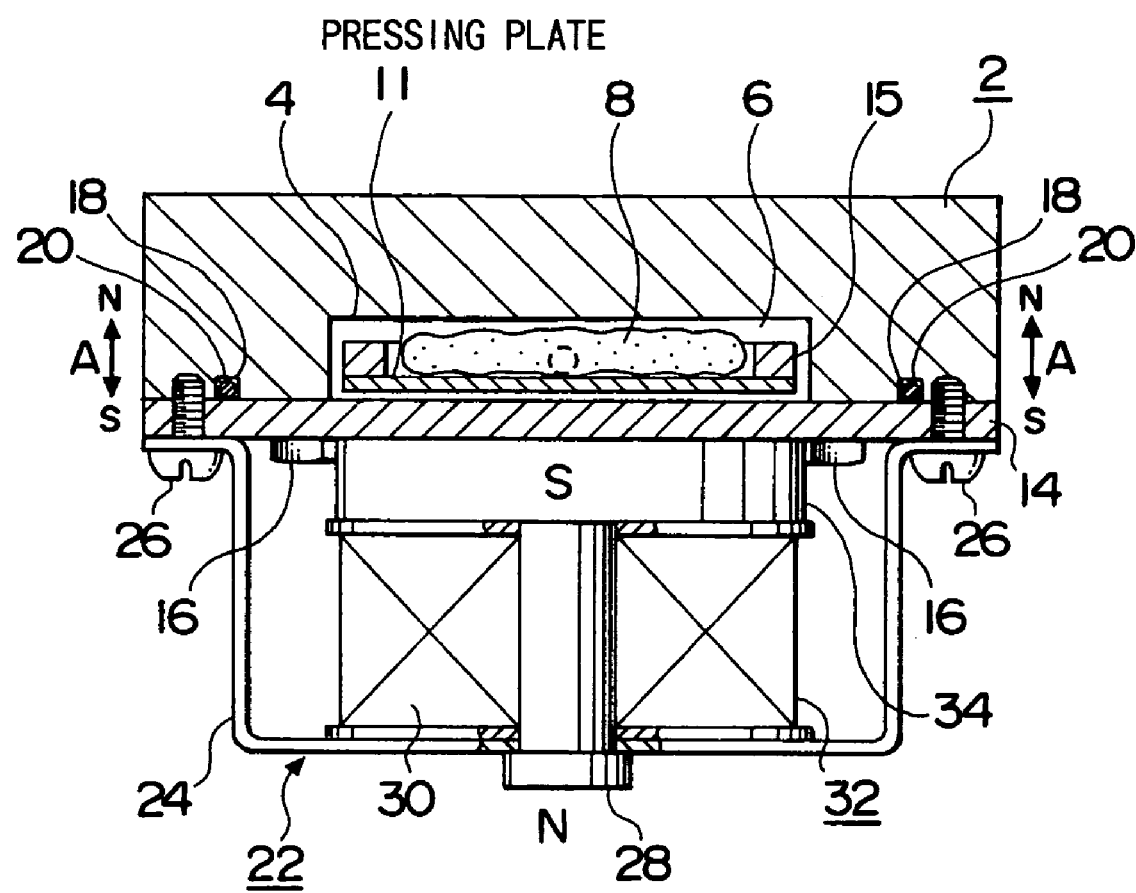
FIG. 9 is a longitudinal sectional view showing a second embodiment of a cell/tissue culture apparatus according to the present invention.
Figure 10:
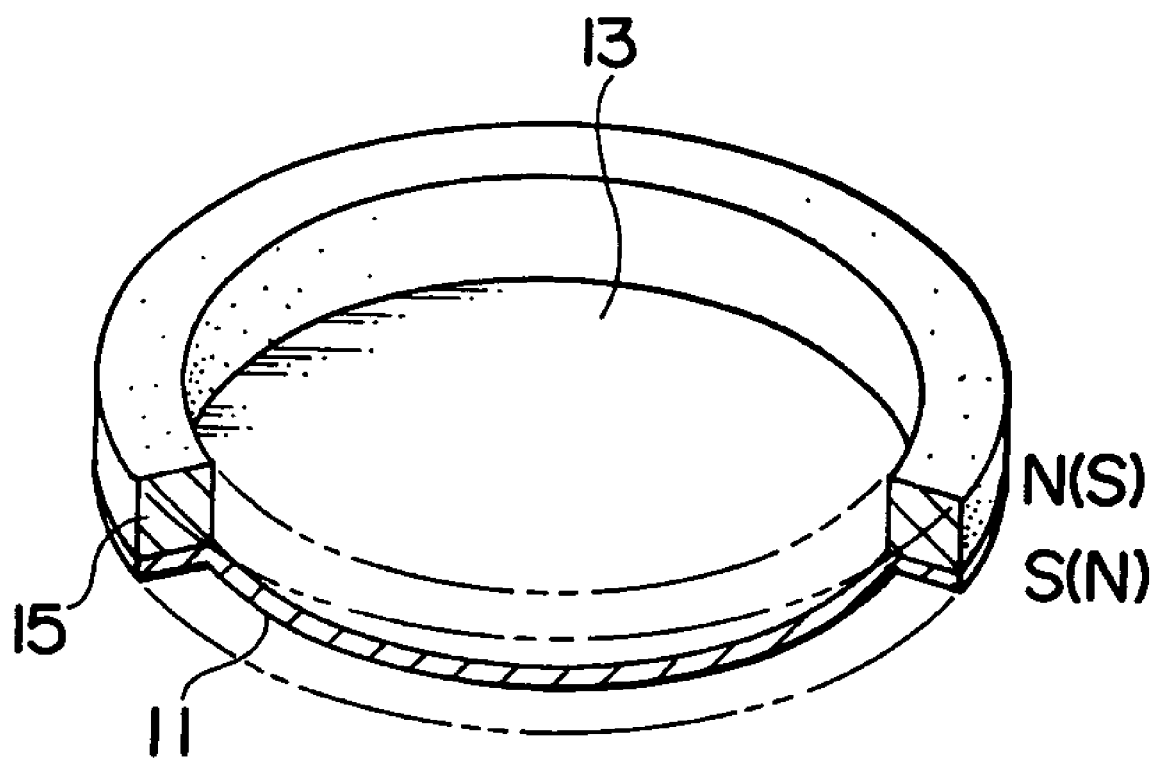
FIG. 10 is a perspective view showing a pressing plate of which a part is nicked.

Next, FIG. 9 and FIG. 10 show a second embodiment of a cell/tissue culture apparatus according to the present invention.

In this embodiment, an annular-shaped magnet 15 is provided at an upper face side of a pressing plate 11, and the matrix 8 is arranged in a space portion 13 of an inside thereof. For example, this embodiment is constituted so that the magnet 15 makes its upper face the N pole and makes its lower face the S pole, and so that the S pole is generated in an upper face side of the core 28 side of the electromagnet unit 32. By this, this embodiment is constituted so that a pressing force is applied to the matrix 8 by means of a repulsive force and cancellation thereof, and so that compression of the matrix 8 and cancellation thereof are performed.

Even if such a composition is given, the culture program shown in FIG. 5 through FIG. 7 can be executed by using the same culture control device 40 shown in FIG. 4.

Further, in this case, if the chamber body 2 is constituted by a transparent material, it becomes possible to visually recognize the inside of the culture chamber 4, and it is possible to observe a culture state of the matrix 8 with ease.

Furthermore, if a state of affairs in the matrix 8 inside the culture chamber 4 is caught as image information by using an imaging means such as a video camera and a digital camera not shown in the drawing, and if the state of affairs in the matrix 8 is observed through the image information, it is possible to visually catch a state of affairs in proliferation and growth of the matrix 8. By this, it is possible to accurately grasp the stages of growth, and it is possible to take exact measures according to a state of affairs in a culture.

According to the cell/tissue culture apparatuses mentioned above, it is possible to give a physical stimulation by compression due to a desired pressing force or by cancellation thereof to a cell or tissue to be cultured, and it is possible to promote a culture.

The configurations, the actions and the effects as the modes for carrying out the present invention are described by referring to the embodiments shown in the drawings. However, the present invention is not limited to the modes for carrying out the present invention and the embodiments mentioned above. The present invention includes all configurations which can be predicted or conjectured by a person skilled in the art, namely, various kinds of compositions, modified examples, and so on, which are conjectured from the objects of the invention, the modes for carrying out the invention, and the embodiments of the invention.

INDUSTRIAL APPLICABILITY

As described above, the cell/tissue culture apparatus according to the present invention can give a physical stimulation by compression due to a desired pressing force or by cancellation thereof to a cell or tissue to be cultured, can make a culture promote, and is useful for a culture of a cell or tissue of a human body.

The invention claimed is:

1. A cell/tissue culture apparatus, comprising:
   a chamber formed in a main body of said apparatus, maintaining an air-tightness, accommodating a culture object, and storing culture fluid to be supplied to said culture object;
   a culture fluid port formed in said main body, opened to said chamber and circulating said culture fluid into said chamber to supply said culture object wit said culture fluid;
   a pressing plate disposed inside said chamber and used for pressing said culture object in said culture fluid; and
   a driving means giving driving force to said pressing plate by means of a magnetic force applied from an outside of said chamber in a state out of contact with said pressing plate and making said pressing plate move to a side of said culture object to apply a compressive force to said culture object from said pressing plate.

2. The cell/tissue culture apparatus of claim 1, wherein said pressing plate provides a magnetic annular portion that receives a magnetic force generated from said driving means, and a driving force is given to said magnetic annular portion by said magnetic force.

3. The cell/tissue culture apparatus of claim 1, wherein a magnetic annular portion provided to said pressing plate and said driving means installed outside said chamber are coupled magnetically, a magnetic force generated by a current level flowing through a solenoid of said driving means is adjusted, and a desired driving force is given to said pressing plate.

4. The cell/tissue culture apparatus of claim 1, wherein a transparent portion is provided to a part or the whole of a wall face portion of said chamber, and said cultured object of an inside of said chamber is made it possible to be visually recognized from an outside of said chamber through said transparent portion.

* * * * *

UNITED STATES PATENT AND TRADEMARK OFFICE
CERTIFICATE OF CORRECTION

| | | |
|---|---|---|
| PATENT NO. | : 7,144,726 B2 | |
| APPLICATION NO. | : 10/499304 | |
| DATED | : December 5, 2006 | |
| INVENTOR(S) | : Takao Takagi et al. | |

It is certified that error appears in the above-identified patent and that said Letters Patent is hereby corrected as shown below:

On the Title Pg Assignee Item (73):

"Takagi Industrial Co." should read -- TAKAGI INDUSTRIAL CO., LTD.--

Signed and Sealed this

Twenty-third Day of January, 2007

JON W. DUDAS
*Director of the United States Patent and Trademark Office*